(12) United States Patent
Rogers et al.

(10) Patent No.: US 7,649,629 B2
(45) Date of Patent: Jan. 19, 2010

(54) OPTICAL IMAGING APPARATUS WITH SPECTRAL DETECTOR

(75) Inventors: John Rogers, Canterbury (GB); Mark Hathaway, Canterbury (GB)

(73) Assignee: OTI Ophthalmic Technologies, Inc. (CA)

( * ) Notice: Subject to any disclaimer, the term of this patent is extended or adjusted under 35 U.S.C. 154(b) by 0 days.

(21) Appl. No.: 11/868,162

(22) Filed: Oct. 5, 2007

(65) Prior Publication Data

US 2008/0088852 A1    Apr. 17, 2008

(30) Foreign Application Priority Data

Oct. 5, 2006    (GB)    ................... 0619616.6

(51) Int. Cl.
*G01B 9/02*    (2006.01)
(52) U.S. Cl. .................................... 356/479
(58) Field of Classification Search ................. 356/477, 356/479, 497
See application file for complete search history.

(56) References Cited

U.S. PATENT DOCUMENTS

2006/0158655 A1* 7/2006 Everett et al. ............... 356/479
2007/0046948 A1* 3/2007 Podoleanu et al. .......... 356/497
2007/0115481 A1* 5/2007 Toth et al. .................... 356/511

OTHER PUBLICATIONS

Apaptive optics parallel spectral domain optical coherence tomography for imaging the living retina, Zhang et al, Optics Express, vol. 13 No. 12, Jun. 13, 2005.*
"Overlay of conventional angiographic and en-face OCT images enhances their interpretation," BMC Ophthalmol 2005;5:12; Van Velthoven M E J, Verbraak F D, Garcia P M, et al.*

* cited by examiner

*Primary Examiner*—Tarifur Chowdhury
*Assistant Examiner*—Jonathon D Cook
(74) *Attorney, Agent, or Firm*—Lawrence E. Laubscher, Jr.

(57) ABSTRACT

Apparatus for obtaining depth profile information from a transparent object, includes a confocal scanner for producing an en-face image of the object in an x-y plane, a spectral optical coherence tomography (OCT) apparatus for producing an OCT scan along at least one line in the z direction passing through a point in the x-y plane, and a display device. A processing unit displays on the display device the en-face image and an indication of the position of the point so as to permit the location of the OCT scan to be determined on the en-face image. The position point can be adjusted by the user when viewing the image. In other embodiments, SLO and OCT images are produced from a common aperture, and spectral OCT images are produced simultaneously with fluorescence images.

13 Claims, 8 Drawing Sheets

OPTICAL IMAGING APPARATUS WITH SPECTRAL DETECTOR

FIELD OF THE INVENTION

This invention relates to optical imaging apparatus, and more particularly to optical coherence tomography imaging apparatus with a scanning laser ophthalmoscope (SLO) or more generally a confocal scanner.

BACKGROUND OF THE INVENTION

Optical coherence tomography (OCT) is a technique for obtaining high resolution information about the internal structure of a transparent object, such as the retina of the eye. The object is scanned with a laser beam from an interferometer. The scanning beam is typically generated by an interferometer with a broadband light source so that the coherence length of the light is relatively short, typically in the order of 2 microns. In time domain OCT, image information is generated from the region, known as the coherence gate, where the optical path difference between the reference beam and object beam is such that it is length than the coherence length of the light. By changing the optical path difference to move the coherence gate in the depth direction, it is possible to obtain image information from the object in this direction. A simple line scan in the z direction is known as an A scan, a two-dimensional or cross-sectional scan in the z-direction, so as to obtain a vertical or horizontal slice extending in the depth direction, is known as a B scan, and an en-face scan across the object is known as a C-scan.

While optical coherence tomography produces very high resolution images in the depth direction, it is difficult to relate the OCT imaging position with an overall view of the eye. For this purpose it is known to superimpose an SLO (scanning laser ophthalmoscope) image on the OCT image. An SLO en-face image is generated by a confocal scanner and while giving poorer resolution than the OCT image gives a more recognizable image of the retina of eye. The SLO image can be used to guide the OCT examination and permit the user to register precisely where the OCT image was taken on the eye fundus.

In conventional time-domain OCT imaging, it takes in the order of ½ second to obtain an OCT frame for a typical B-scan. The SLO image can be generated in about ½ second. The delay in creating the OCT image leads to inaccuracies in the registration of the OCT image against the SLO image because of potential movement of the eye fundus between the creation of the images. One possible solution to this problem is to use a full-field flash image instead of an SLO image. While this process captures the whole image area at once, it cannot be used continuously and lacks the versatility of SLO imaging for registration purposes.

Typically, such combined systems that employ both a confocal and OCT scanner involve complex optics. Alternatively, it is possible to derive a pseudo confocal image in software from the OCT signal, but such an image is not as good as a true confocal image since it depends on the OCT signal, and multiply backscattered light does not contribute to the OCT signal.

Fluorescence imaging is a technique that is commonly used in the imaging of biological samples. For example, it can be used to study biological processes occurring within the retina. In fluorescence imaging, the sample is illuminated with a light of one wavelength, which causes fluorophores, such as ICG (indocyanine green) in the sample to fluoresce at a different wavelength from the illuminating light. The fluorescent light is detected and used to form an image, which gives information about internal biological processes occurring within the sample.

Fluorescence imaging can be combined with an OCT image to look at biological processes within the eye in the context of a three dimensional scan of the eye. While it would be desirable to produce a scan covering a three dimensional volume of the sample at the same time as a fluorescent image is produced, this is not possible with conventional time domain OCT imaging because of the time it takes to create an OCT three dimensional image. The fluorescence image is created as a raster scan of the surface of the object in the x-y plane. It is not possible to simultaneously obtain depth imaging for the whole image and a fluorescence image using conventional time domain OCT technology due to time constraints.

SUMMARY OF THE INVENTION

The present invention provides an OCT imaging system in which the accuracy of registration between the OCT image and the SLO image is remarkably improved.

According to the present invention there is provided an apparatus an optical imaging apparatus for obtaining depth profile information from a transparent object, comprising a spectral optical coherence tomography (OCT) apparatus for generating a sample beam for transversely scanning said object; a spectrometer for producing spectral OCT data from light returned from said object along at least one line extending in a longitudinal direction; a confocal detector for producing an en-face image of the object in a transverse plane from said sample beam; a processing unit generating from said spectral data OCT image data along said at least one line; said processing unit being configured to display said en-face image; a selector for selecting a portion of said en-face image; and said processing unit being configured to display said portion of said OCT image data corresponding to said portion of said en-face image.

In accordance an embodiment of the invention, the confocal scanner and OCT scanner employ a common aperture.

In another aspect the invention provides optical imaging apparatus comprising an interferometer for generating a sample beam; a scanner for scanning a transparent or semi-transparent object with said sample beam; a coupler for combining the sample beam returned from the object with a reference beam to produce respective output beams at a pair of output ports; a confocal detector at one of said output ports; and a spectrometer at the other of said output ports for producing a spectral OCT signal. The invention permits a real confocal image and an OCT image to be constructed from the output of the interferometer, thus obviating the need for separate optics to handle the OCT imaging. The invention thus offers substantial advantages over the prior art, which either employs complex optics or does not produce a true confocal image from the beam returned from the sample.

In yet another aspect, the invention combines fluorescence imaging with spectral OCT imaging in a way that permits quasi simultaneous images to be obtained. Each raster line of the fluorescence image is associated with an OCT B-scan obtained in real time.

According to another aspect of the invention there is provided optical imaging apparatus comprising an interferometer for generating a beam to scan a sample in a raster pattern; a fluorescence detector for producing a signal from fluorescent light produced within the sample; a spectrometer for deriving an OCT (optical coherence tomography) signal from beam returned by the sample; a processor for producing fluorescent image frames from the signal produced by the fluorescence detector and OCT cross sectional images (B-scans) behind each scanning line of the raster pattern, said OCT cross sectional images being obtained by analyzing the spectral composition of the beam returned by the sample; and a display for displaying the fluorescence images and OCT cross sectional images in association with the corresponding fluorescence images.

It will be understood that the terms optical and light do not restrict the invention to the visible spectrum, but may include infrared and ultraviolet in accordance with common usage in the art.

In addition to using a broadband source to obtain the spectral OCT data, it is also possible to use a swept source wherein the wavelength of the source is rapidly changed over the wavelength range of interest.

DETAILED DESCRIPTION OF THE PREFERRED EMBODIMENTS

Figure 1:
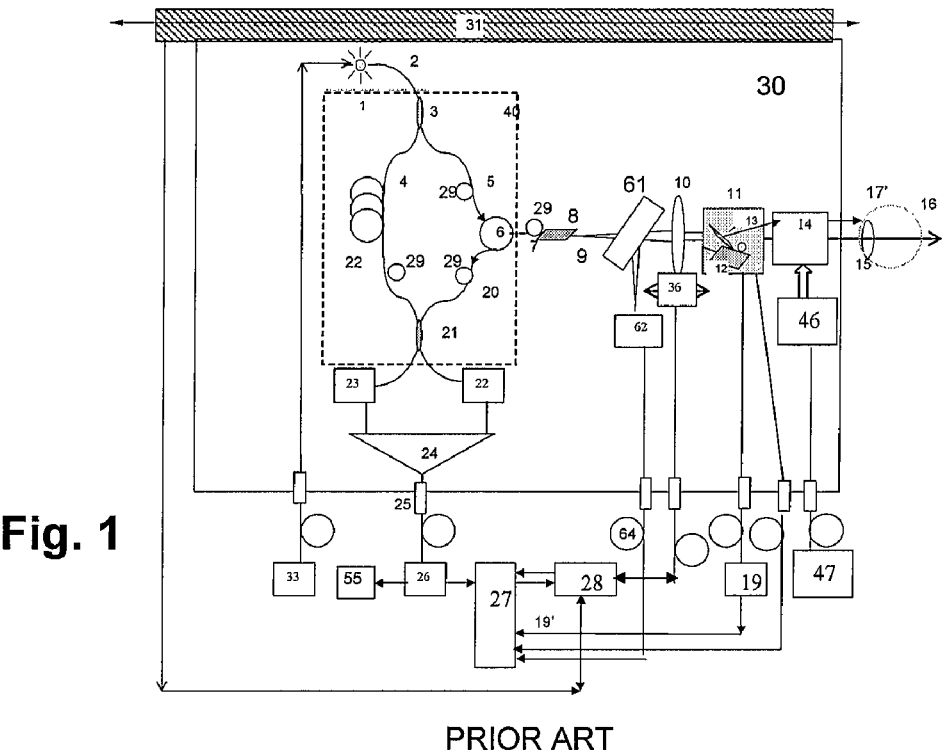
FIG. 1 shows a prior art apparatus with confocal scanner using time domain optical coherence tomography.

FIG. 1 shows a typical prior art time domain OCT apparatus with confocal scanner (SLO) for producing simultaneous confocal and OCT images. The apparatus comprises an optical source 1, which can be either low coherence or with adjustable coherence length, pigtailed to a single mode fiber, 2, wherefrom the power is split in a first optical splitter, which in FIG. 1 is shown as a directional single mode coupler, 3, into a reference beam, along the reference path 4 and an object beam, along the object path, 5. Light into the object path 5 is launched from the $1^{st}$ output of the first splitter and light into the reference path 4 is launched from the second output of the first splitter. The light source 1 is controlled by controller 33.

In the context of the invention, a low coherence source is a broadband source, whose coherence length is much less than the penetration depth of the radiation used in the object studied. Examples of such sources include superluminiscent diodes, tungsten lamps, Kerr-lens mode-locked lasers, laser diodes below threshold and diverse combinations of the above. For instance, at the level of the technology today, the coherence length of such sources covers the range of 0.5-500 μm. In contrast, in the context of the invention, a high coherence source has a coherence length much larger than the penetration depth of the radiation used in the object studied. Examples of such sources include lasers, with a coherence length larger than 1 cm.

In the object path, a second optical splitter, 6, which in FIG. 1 is shown as an in-fiber circulator, is used to transfer light from the $1^{st}$ output of the first optical splitter and send light, via path 7 to output 8, terminated with a fiber connector at an angle, or cleaved at an angle, to minimize the fiber end reflection and in this way the noise. From the output 8, the light is sent via free space, 9, towards the focusing element 10, such as a refractive or reflective optical element and then deflected by a 2D scanner head 11, equipped with mirrors 12 and 13 to scan transversally, via interface optics 14, an object.

In FIG. 1 the object is either the cornea 15 or the retina 16 of an eye 17, in which latter case the beam is focused by the cornea 15 and eye lens 18 onto the retina 16. The object could be any other type of tissue or industrial object, such as powder or lenses to be tested, such object being placed where cornea 15 or the retina 16 are shown in FIG. 1. The line connecting the transverse scanning means and the object constitutes an optic axis of the apparatus, oriented along the deflected object beam in the middle of the scanning range of the transverse scanning means.

Scanner head 11 is a scanning assembly means known in the art and includes, for example, galvanometer scanners, piezo-vibrators, polygon mirrors, resonant scanners, acousto-optic modulators, rotating or vibrating prisms etc. Combinations of scanners from the list above can be used for the scanning pair head 11. One scanner usually works fast and the signal collected during its movement is displayed on the line in the raster of the final image, termed as the line scanner, while the other scanner, is typically termed as frame scanner. For instance, a polygon mirror can be used as the line scanner and a galvanometer scanner can be used as the frame scanner. The scanner head 11 is under the control of triangle, sawtooth or DC voltages produced by a generator 19.

The scanning head 11 is divided in two parts, namely the line scanner and the frame scanner, separated by optical elements such as lenses and/or mirrors in configurations known in the art of scanning laser ophthalmoscopes (SLO) and of confocal microscopy or general raster scanning systems. The scanner mirrors 12 and 13, which refer to either galvanometer scanners or polygon mirrors have high reflectivity at the wavelength used, or if acousto-optic modulators are used, their transmission at the wavelength used is high. By means known in the art, the two scanners have orthogonal axes or scan the ray in perpendicular planes, producing a raster in the plane (X,Y), oriented perpendicular on the optic axis of the system. Circular scan, $(\rho,\theta)$ of the ray can also be obtained by sinusoidally scanning the ray using the two scanners in orthogonal directions at the same frequency with a phase difference of $\pi/2$, where $\rho$ is determined by the amplitude of the angular deviation, measured in a plane perpendicular on the optic axis from the point hit by the ray when the scanners are not driven, and $\theta$ is a polar angle in this same plane.

Light returned from the object, via the interface optics 14, and then via the scanning head 11, is launched via the focusing elements 10 back into the second optical splitter 6, that is into the same port fiber, 7 of the circulator, 6, where the light originated from. The circulator routes the signal to the fiber output 20, which takes the signal to a first input of a third optical splitter 21, which in FIG. 1 is shown as a single mode directional coupler. The second input of the optical splitter 21 receives light from the reference path, 4, via a fiber delay line 22. The object signal interferes with the reference signal when the optical path difference (OPD) between the reference path length and the object path length is less than the coherence length of the source 1. This explains the selection in depth of the OCT. The reference path starts at the optical splitter 3 and ends at the optical splitter 21, and is made of fiber 4 and delay line 22. The object path starts from the optical splitter 3 and again ends on the optical splitter 21, made out of fiber 5, circulator 6, fiber 7, fiber connector 8, free space path 9, focusing element 10, scanner head 11, interface optics 14 up to the object and back to the fiber 7. Points along the object beam in the volume of the object will contribute to the signal only from within the coherence length of the source in the volume of the object. The embodiment in FIG. 1 has the advantage that the reference beam is all in fiber and no losses are incurred due to passing the light from fiber to free air and back, to allow for the adjustment of the reference path length.

To maximize the interference signal, polarization of light in the two arms of the interferometer needs to be the same. Therefore, at least a polarization controller 29 in one of the object path or reference path is required.

In time domain OCT, the optical splitter 21 is typically terminated on two photodetectors 22, 23 of a balanced photoreceiver unit 24. The photodetected signal obtained at the electrical connector output, 25, of the unit 24 is sent to the processing block 26 to provide strength proportional to the reflectivity, or the log version of the reflectivity, and then displayed and recorded by means of a suitable display device 27, such as a frame grabber, a storage oscilloscope or a suitable printer. The device 27 is under the control of computer 28. The block 26 contains a band pass filter followed by a rectifier and a low pass filter.

The filter is adjusted on two different functions depending on the regime of operation of the apparatus, as described below.

All the elements within the dashed contour 40 belong to the core interferometer. All the elements within the block 30 can be moved together by the stage 31.

Optionally, when the object is the eye, a fixation lamp unit, 46, interleaved with the interface optics 14, is used for sending light towards the eye for guidance of the patient. Such a fixation lamp uses a beamsplitter or a dichroic filter by means known in the art to conveniently send light from a visible source to the eye, and move this source laterally by mechanical means, or by using a liquid crystal or a 2D LED array to move a spot, a cross or a star or a shaped luminous point laterally by electric means. The fixation lamp is powered by a power supply 47.

The lens 10 and interface optics 14 can be implemented using reflective elements or combination of refractive and reflective elements. The signal driving the transverse scanner may have other forms different from triangle or sinusoid and the only essential feature for this operation is that the signal is periodic.

A confocal optical splitter, 61 is placed in the object path 9 leading to the focusing element 10. This diverts some of the light returned from the object 15 or 16 to a confocal receiver, 62. A confocal receiver is implemented using a pinhole and a high gain photodetector amplifier, equipped with an avalanche photodiode or a photomultiplier, by means known in the art and described in the copending application "Optical mapping apparatus with adjustable depth resolution and multiple functionality", by A. Gh. Podoleanu, J. A. Rogers, G. Dobre, R. Cucu, D. A. Jackson, U.S. Pat. No. 6,769,769, the contents of which are herein incorporated by reference. In this embodiment the splitter 61 and confocal receiver 62 are mounted on the same stage 30 as the other optical elements and moved together. A flexible coaxial cable, via connector 63 and loop 64 delivers the signal from the output of the confocal receiver channel to the displaying means 27, which could be implemented for example by a two input digital frame grabber under the control of the PC control 28.

Preferably, the splitter 61 is a plate beam-splitter, sufficiently thick to avoid multiple reflections being returned to the fiber end 8, as explained in the co-pending application "Optical Mapping Apparatus with Optimised OCT Configuration", by Adrian Podoleanu, George Dobre, Radu Cucu, John Rogers, David Jackson, USA Application, May 2003, number unknown. This splitter has an optimum splitting ratio as explained in the U.S. Pat. No. 5,975,697 to insure similar signal to noise ratios in the two channels, OCT and confocal. The splitting ratio could be found experimentally as 1 to 18% power diverted to the confocal receiver 62 from the power returned from the object 15 or 16.

The confocal splitter 61 is used in transmission by the OCT signal and reflection by the confocal channel, however of course the optical splitter 61 can be used in transmission by the confocal signal and in reflection by the OCT signal.

The above described apparatus permits the quasi-simultaneous display of OCT and confocal images, but as noted above because of the time delay, difficulties arise in making a direct comparison between the OCT and confocal images.

Figure 2:
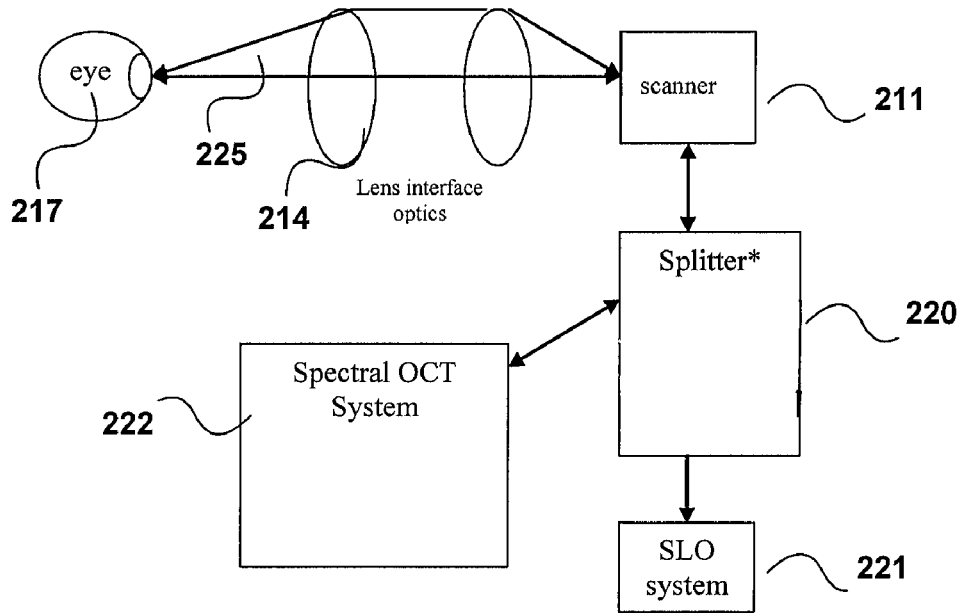
FIG. 2 is a simplified diagram of an embodiment of the invention using a confocal scanner and spectral detector.

In accordance with an embodiment of the invention, as shown in FIG. 2, a spectral OCT detector is employed. As in the case of the apparatus shown in FIG. 1, the eye 217 is scanned with object beam 225 from interface optics 214 and scanner 211. However, the returned beam is passed to splitter 220, which diverts some of the light returned from the eye to spectral OCT system 222. The remaining light is passed to the SLO system 221, where a confocal image is generated.

In FIG. 2, the splitter 220 is shown as a separate component to the spectral OCT system, but it will be understood that the splitter can be embedded within the interferometer. For the most effective signal-to-noise ratio, the diversion of light returned from the eye should take place before the returned object beam is mixed with the reference light.

Figure 3:
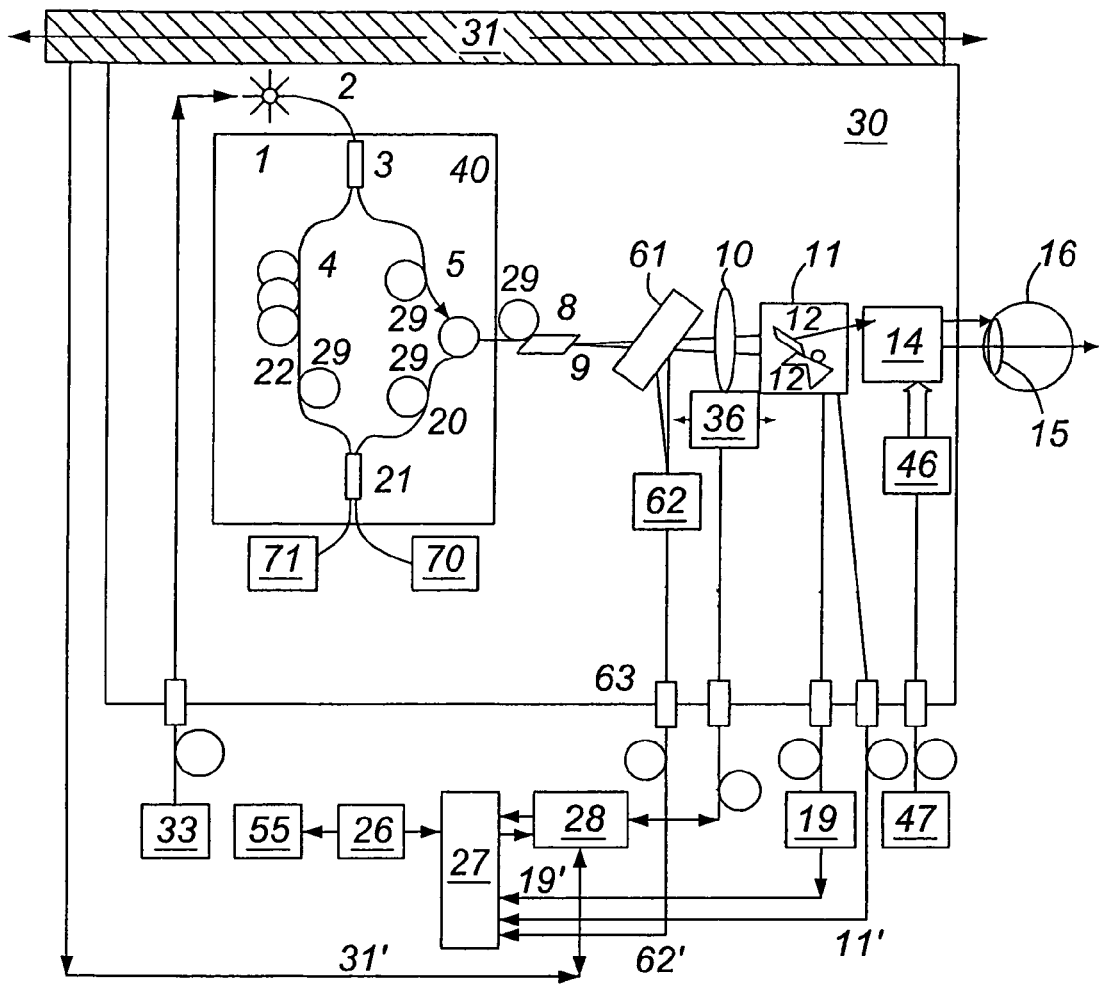
FIG. 3 is a diagrammatic view of a more detailed implementation of an embodiment of the invention.

Conveniently, as shown in FIG. 3, the photodetectors 22 and 23 of FIG. 1 can be replaced by a single spectrometer 70 connected to processing block 26. The confocal and OCT images can be displayed on the display 55 in a similar manner to the apparatus shown in FIG. 1. For example, the images can be displayed in an overlaid manner or one above the other so that the correspondence between the features in the OCT image and confocal image can be observed.

Alternatively, an identifier can be indicated on the confocal image at the point (in the case of an A scan) or line (in the case of a B-scan) where the corresponding OCT data is obtained.

The location of the OCT image displayed can be adjusted with the computer 28. In one preferred embodiment, the computer stores a three dimensional image data set, so that by pointing to a particular feature on the SLO image with a mouse, for example, the operator can select and direct the computer to display an OCT image corresponding to a particular point or line on the corresponding displayed SLO image.

Alternatively, where the sequential images are displayed sequentially, the computer can direct the OCT imaging system to obtain a frame along a line (A-scan) or frame (B-scan) at the point or line indicated on the screen. In the case of a B-scan, cross hairs can be provided on the screen to select a particular line along which the B-scan section is desired. The computer 28 then directs the scanner to obtain a B-scan along that line. It is only necessary to perform one scan across the object because for each surface image point, the spectral OCT equipment produces a complete line of data extending in the z direction.

The spectrometer 70 produces an output signal which is effectively the Fourier transform of the intensity distribution in the z or depth direction. Essentially, this system performs OCT in the Fourier domain. By analyzing the spectrum of the returned beam after it interferes with the reference beam, it is possible to derive an A scan extending in the z direction from the spectral distribution of the light without the need to move the coherence gate as is the case for time domain OCT. This is explained in more detail in the article by A. F. Fercher, C. K. Hitzenberger, G. Kamp, S. Y. El-Zaiat: Measurement of Intraocular Distances by BackscatteringSpectral Interferometry, Opt. Commun. 117 (1995) 43-48, and U.S. Pat. No. 6,377,349, the contents of which are herein incorporated by reference. Briefly, in the case of an interferometer with a fixed path length difference between the two arms, for some particular wavelength this fixed path length difference will give rise to totally destructive interference of the mixed light field, assuming the two arms of the interferometer are balanced. If this wavelength is allowed to change with the path lengths still fixed, the change in wavelength will produce a sinusoidal variation in the signal that is the result of mixing the light from the two arms of the interferometer.

For a fixed position of the reference mirror and a fixed point on the sample, the broadband light which is reflected from a given point within the sample will produce a sinusoidal pattern within the spectrometer when it is mixed with light from the reference arm. The frequency of the sinusoidal spectrometer signal will encode the depth. The amplitude will encode the reflection coefficient of the point being considered. Light that is back-reflected along the path of illumination will have a characteristic frequency and amplitude at each point within the spectrometer. Applying a discrete fast Fourier transform to the spectrometer signal provides a complete A-scan of the sample without the need to move a coherence gate as is necessary in the case of time domain OCT.

Figure 4:
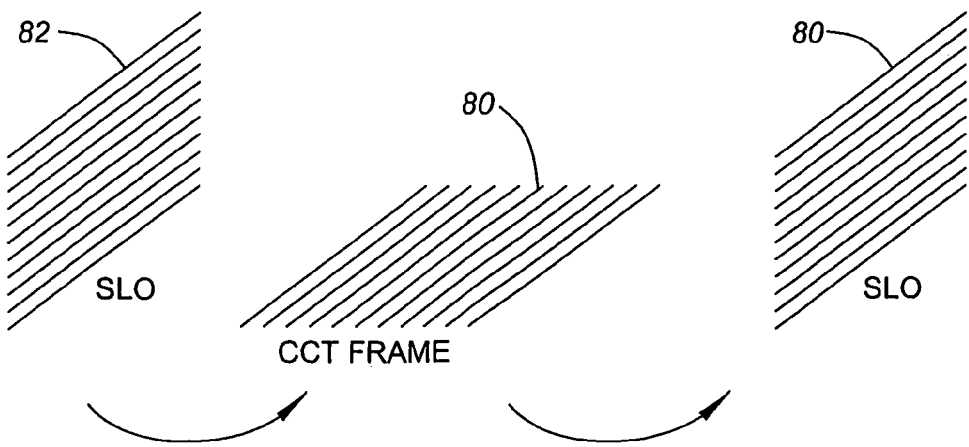
FIG. 4 illustrates the frame sequence of OCT and confocal images.

As shown in the embodiment of FIG. 4, the OCT frame 80 is obtained between the confocal frames 82. The confocal scans are obtained using a conventional flying-spot system and produce a transverse en-face scan of the object, in this case the retina of the eye. Using the galvoscanner system described, the SLO images typically take about ¼ second. Using spectral OCT, the OCT frame can be obtained in about 1/100 to ¼ seconds. As a result the registration accuracy of the OCT and confocal image is much improved.

Figure 5:
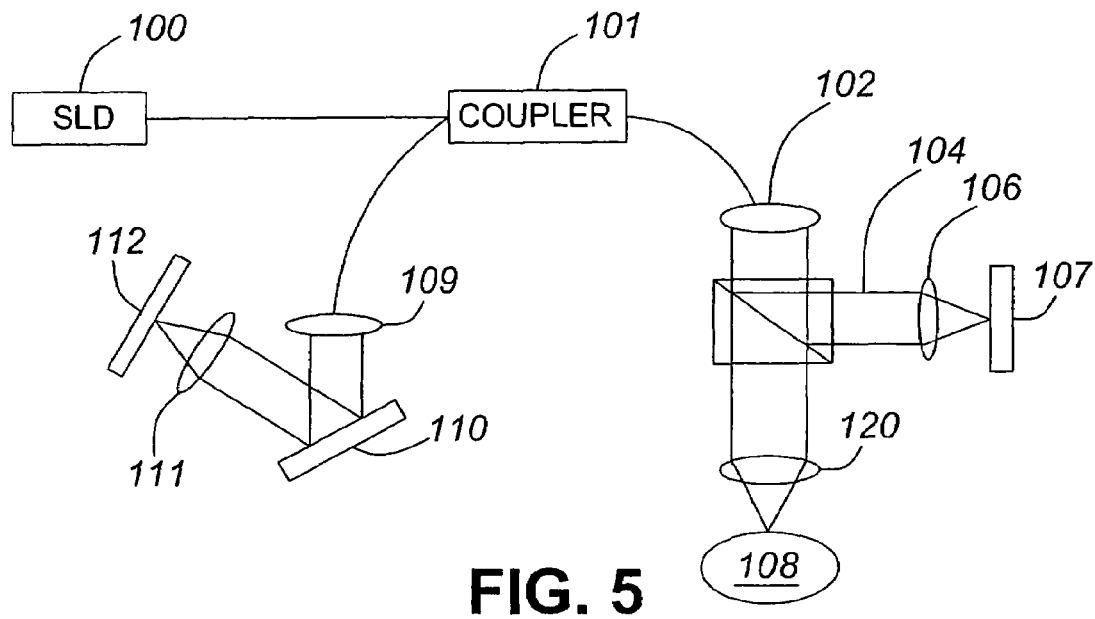
FIG. 5 is a simplified schematic diagram of spectral OCT scanner.

FIG. 5 is a simplified view of a spectral OCT interferometer. In this embodiment, light source 100 directs light beam through a coupler 101 to a collimating lens 102. The output of the lens 102 is split by beam splitter 103 into reference arm 103 and object arm 104. The sample beam is returned mirror 107 and lens 106. The object arm passes through the lens 120 to sample 108.

The light source 100 with a broad range of wavelengths is split into two parts. One part is delivered to the sample, and the same optical path used to deliver the illumination light is also used to collect the signal light that is backscattered or reflected by the sample. The other part is delivered to a reference arm which is subsequently mixed with the light collected from the sample. In a classic Michelson interferometer the interference pattern is produced by varying the length of one of the interferometer arms. In a Fourier Domain interferometer a variation of the wavelength of the light field gives rise to the interference pattern.

Referring now again to FIG. 3, the processor 26 combines the confocal image produced by the processing block 27 with the spectral OCT image and displays the two simultaneously on the display device 55.

Figure 6:
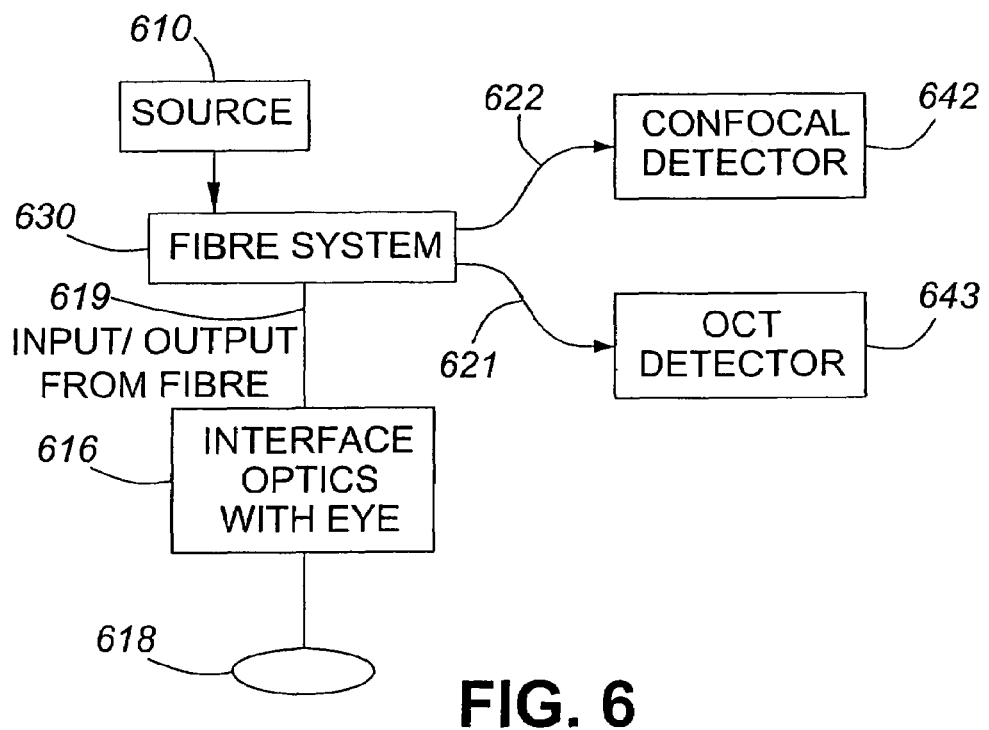
FIG. 6 is a block diagram of a system in accordance with another embodiment of the invention.

FIG. 6 is a block diagram of a system in accordance with another embodiment of the invention, wherein the OCT and confocal system employ a common aperture. Light from the source 610 is input to a fiber optic system 630, wherein it is split in an interferometer into a sample beam and a reference beam. The sample beam 619 is passed to the interface optics 616, typically including the galvoscanner, which scans the sample 618 with the sample or object beam. The scan is typically a raster scan to obtain the confocal image. To obtain the OCT image, the sample beam is maintained at the same point for an A-scan, or moved along a line in the x-y plane, to obtain a B scan.

Figure 7:
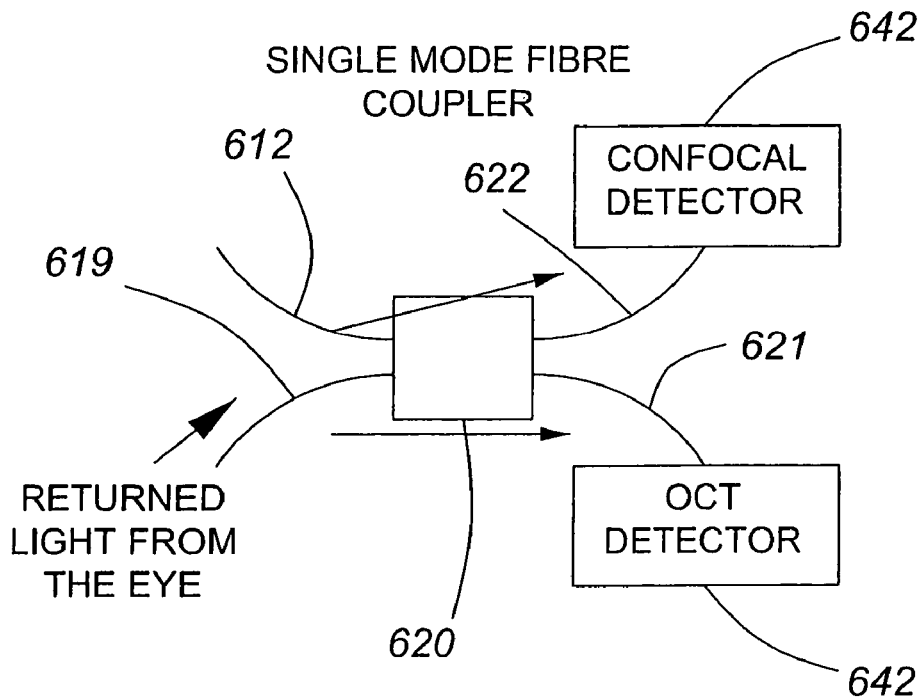
FIG. 7 illustrates the coupler combining the sample and reference beams.

The sample beam 619 (FIG. 7) returned from the interface optics 616 is passed to the fiber optic system 630, where it is combined in the fiber coupler 622 with the reference beam 612 to form the pair of output beams 621, 622 containing the interference information. Instead of terminating in photodetectors 23, 24 of balanced detector 25, as in FIG. 1, the optic fibers carrying the output beams terminate in a confocal detector 642 and an OCT detector 643, which unlike in the prior art is a spectrometer.

The spectrometer 643 produces an output signal which is effectively the Fourier transform of the intensity distribution in the z or depth direction, and as noted above provides both depth and intensity information simultaneously in the z direction.

By attaching spectrometer 70 to one of the output ports of the coupler 21 (See FIG. 3) and a confocal detector 71 to the other, considerable simplification in the construction of the apparatus can be achieved. Much of the optics can be completely eliminated. In this embodiment, the invention takes advantage of what in effect becomes a spare port of the output coupler 21 when the balanced detection unit used in the time domain is replaced by a spectrometer on one of the ports and OCT processing is performed in the Fourier domain.

Figure 8:
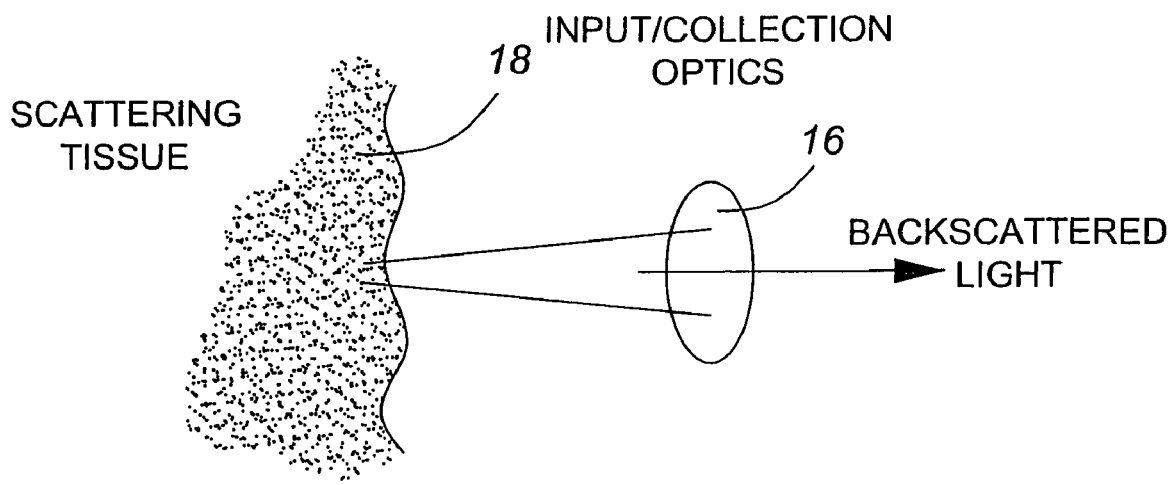
FIG. 8 is a diagrammatic illustration showing the backscattering of light from the sample.

FIG. 8 illustrates the backscattering of incident light on sample 10. It is possible to obtain a pseudo confocal signal in software from the OCT signal, and thus avoid the need for a separate confocal scanner. However, the problem with a software generated confocal signal is that the backscattered light that has been multiply scattered will not contribute confocal signal (or to the OCT spectral signal). On the other hand, it will contribute to the real confocal signal detected by confocal detector 42. Thus, the invention offers a compact solution to obtaining dual confocal/OCT images, wherein the confocal images are real images that take into account multiply scattered light.

Figure 9:
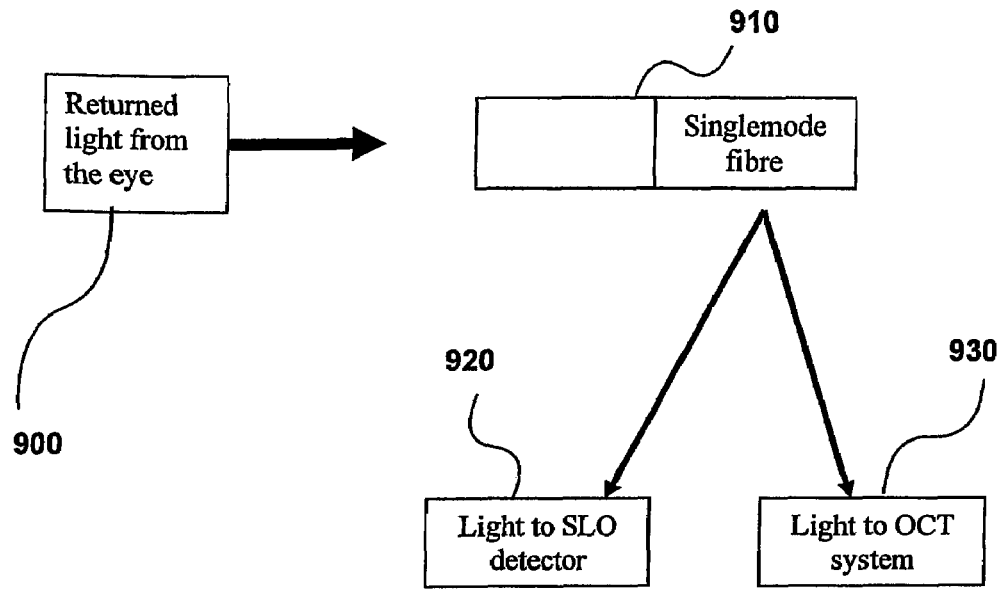
FIG. 9 is a simplified diagram showing a common aperture embodiment.

In the embodiment shown in FIG. 9, light returned from the eye is directed into a single mode fiber, from where it is directed to an SLO detector 920 and an OCT system 930.

Figure 10:
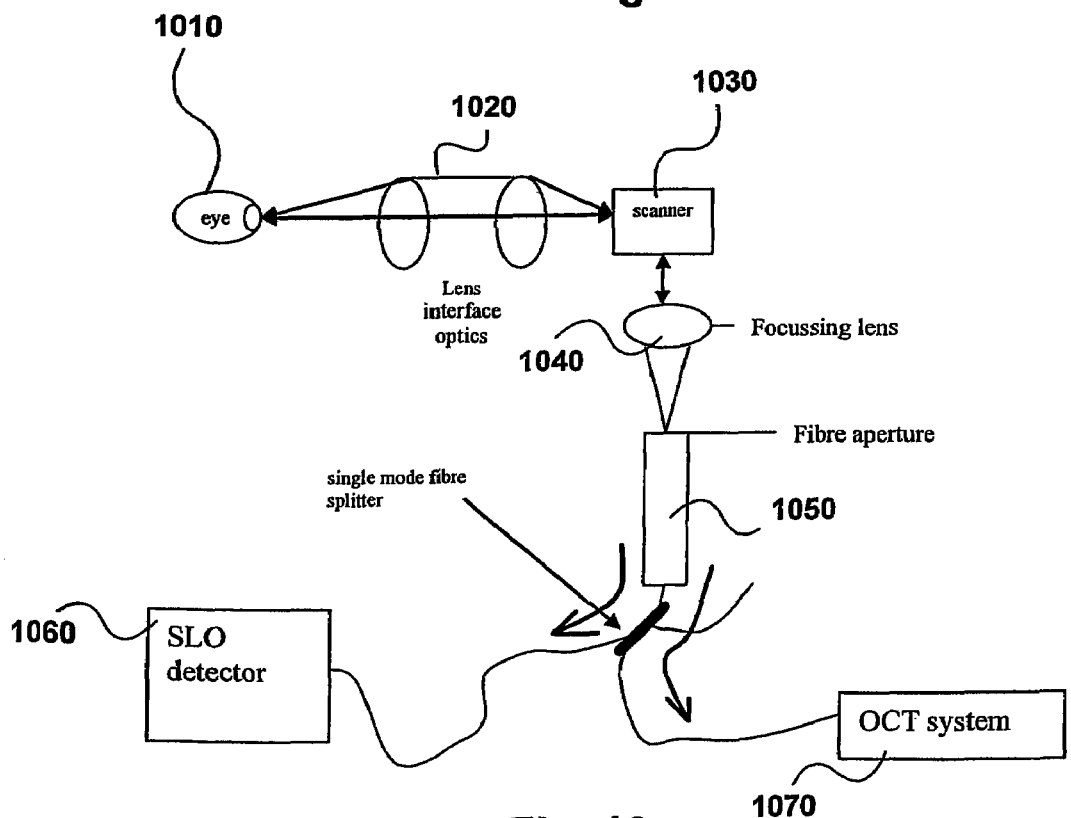
FIG. 10 is an alternative common aperture embodiment.

A more complete system is shown in FIG. 10. Light from the eye 1010 passes through interface optics 1020 to scanner 1030, and from there through focussing lens 1040, from where it is directed into the common aperture of fibre 1050. Upon exiting fiber 1050, the light strikes splitter 1055, from where it is directed to OCT system 1070 and SLO detector 1060.

Using the single mode fibre as the aperture and doing the splitting of some of the returned light from the eye in fibre ensures that the confocal aperture of both SLO and OCT channels is the same. This makes it easier to keep the light in focus.

Whereas the confocal properties of using the fibre are common to both the SLO and OCT capture, the range of where the light has come from within this aperture is dependent on the type of analysis performed on the OCT signal. This fundamental difference and the simultaneous nature of the capture mean that a correlation between the two signals creates a unique diagnostic method. In the SLO channel, the integration time is related to the optical resolution in the sample. Any type of backscattered light contributes to the signal.

In the OCT channel, the light is analyzed in the Fourier domain. The signal is based on the spectral information. The integration time is related to optimum signal-to-noise ratio. Mainly single scattered photons from the sample that contribute to the signal.

In the arrangement shown in FIG. 10, the fiber port used as the collection aperture for the OCT and SLO signals does not necessarily have to be the same as the source of the output of the light for the imaging beam. The focussing lens also could be implemented differently using the lens immediately in front of the eye.

Figure 11:
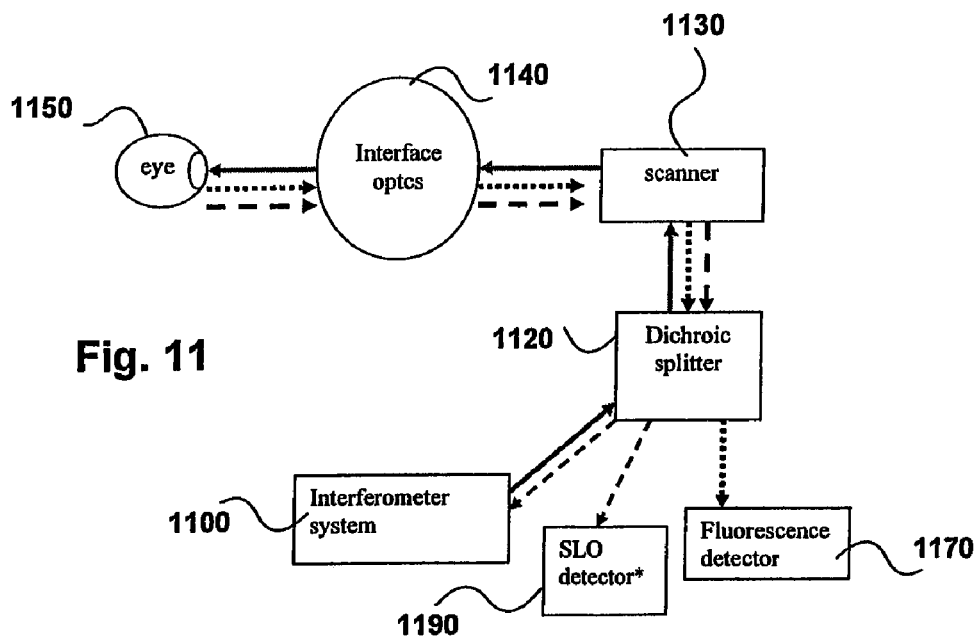
FIG. 11 is an embodiment of an apparatus with fluorescent imaging.

In yet another embodiment of the invention shown in FIG. 11, the invention is applied to fluorescence imaging. The light beam causes fluorophores, typically ICG, in the sample to fluoresce, and by detecting the resulting fluorescent light, a sequence of image frames can be constructed. The sequence of image frames produces a video output, which allows the user to monitor biological processes occurring in the sample in real time.

In this case an excitation beam 110 from interferometer 1100 is passed through a dichroic filter 1120 to scanner 1130, from where it passes through interface optics to eye 1150. The returned fluorescence beam 1160 (dotted line) is pass back through the scanner and dichroic filter to the fluorescence detector 1170. The reflected light 1180 (dashed line) is passed back through the chain to the interferometer 1100 and optionally the SLO detector 1190.

The return OCT beam is detected by a spectrometer, from which information is obtained about the scattering points along the beam in the z direction. At each instant, a line of data is produced in the z-direction from the signal output by the spectrometer. As the raster beam sweeps across the surface of the sample, the depth information derived by the OCT equipment produces a B-scan through the sample. Thus, successive scan lines produce a series of B-scan images containing the scan line and extending back into the sample.

Each complete raster scan or frame of the fluorescent image is thus accompanied by a three dimensional OCT image, which gives complete structural information about the sample in the volume associated with the fluorescent image.

It is possible for the user to view the biological processes occurring in retina by looking at the video comprising the sequence of fluorescence images, and then view cross sections of the sample in different planes to look at the structure of the sample and correlated this with the fluorescence images. For this purpose, the fluorescence images can be superimposed on the OCT sectional images on the same display screen.

When a physician identifies a region of interest from the fluorescence images, which might relate to a particular biological process of interest, the physician can effectively view a series of high resolution cross sectional images through that region as if the physician were to dissect the sample through the region of interest and view the section under a microscope.

The selection of cross sectional images is done under computer control. The physician can also freeze the video so as to show a single frame correlated with the selected cross section.

Figure 12:
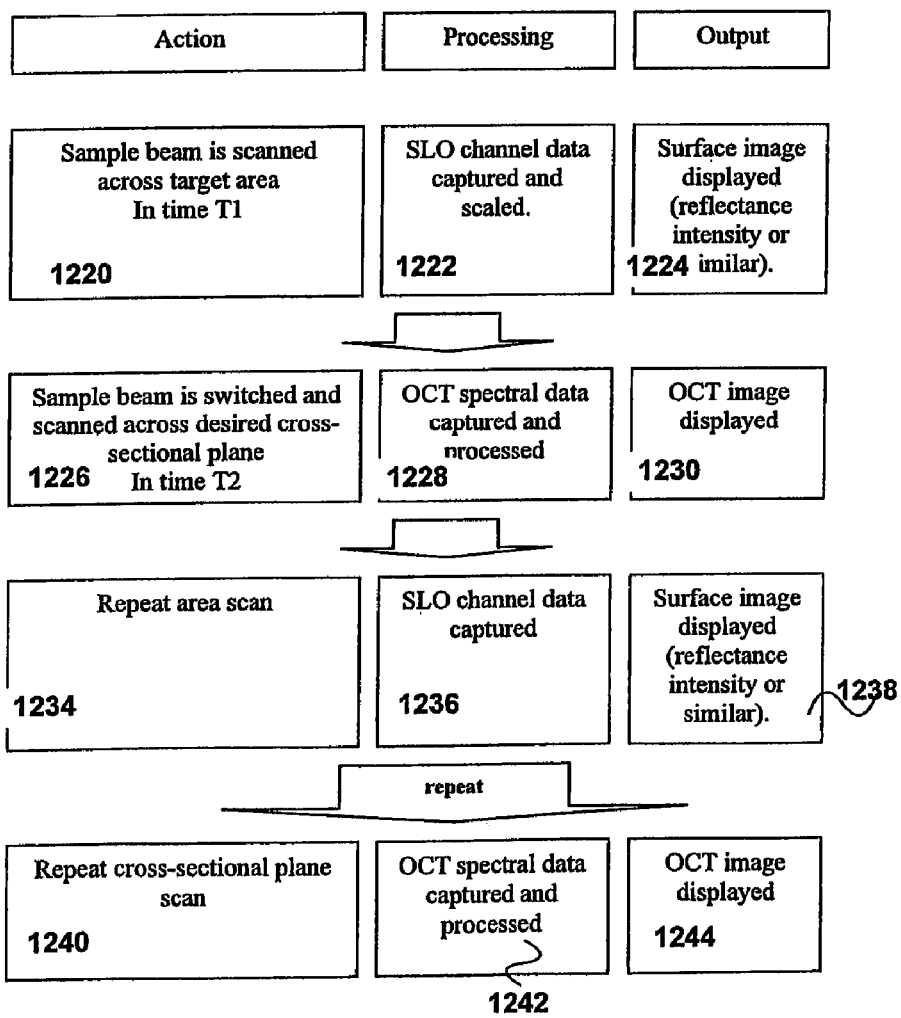
FIG. 12 is a flow chart for sequential SLO and spectral OCT.
Figure 13:
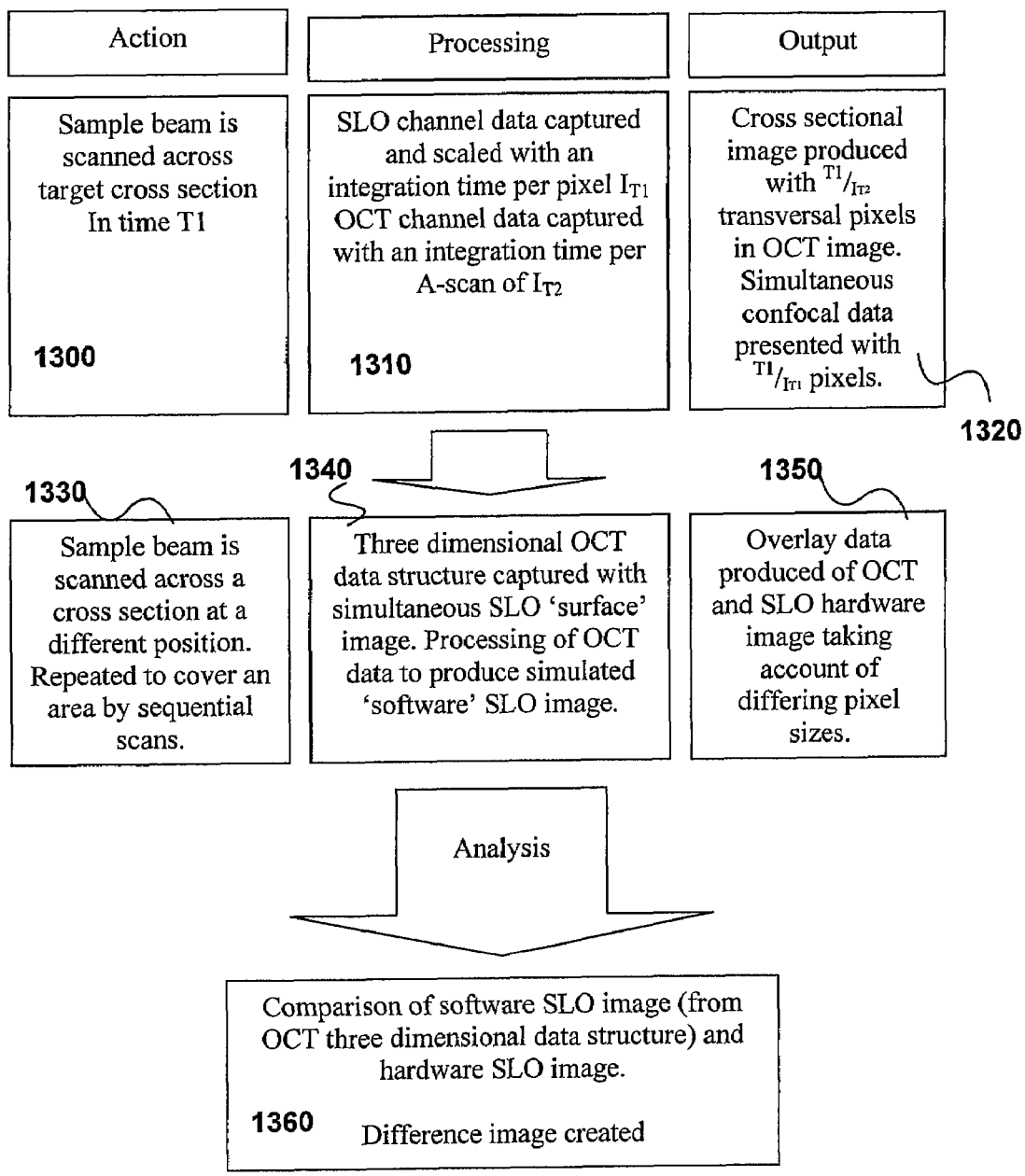
FIG. 13 is a flow chart common aperture SLO and spectral OCT.
Figure 14:
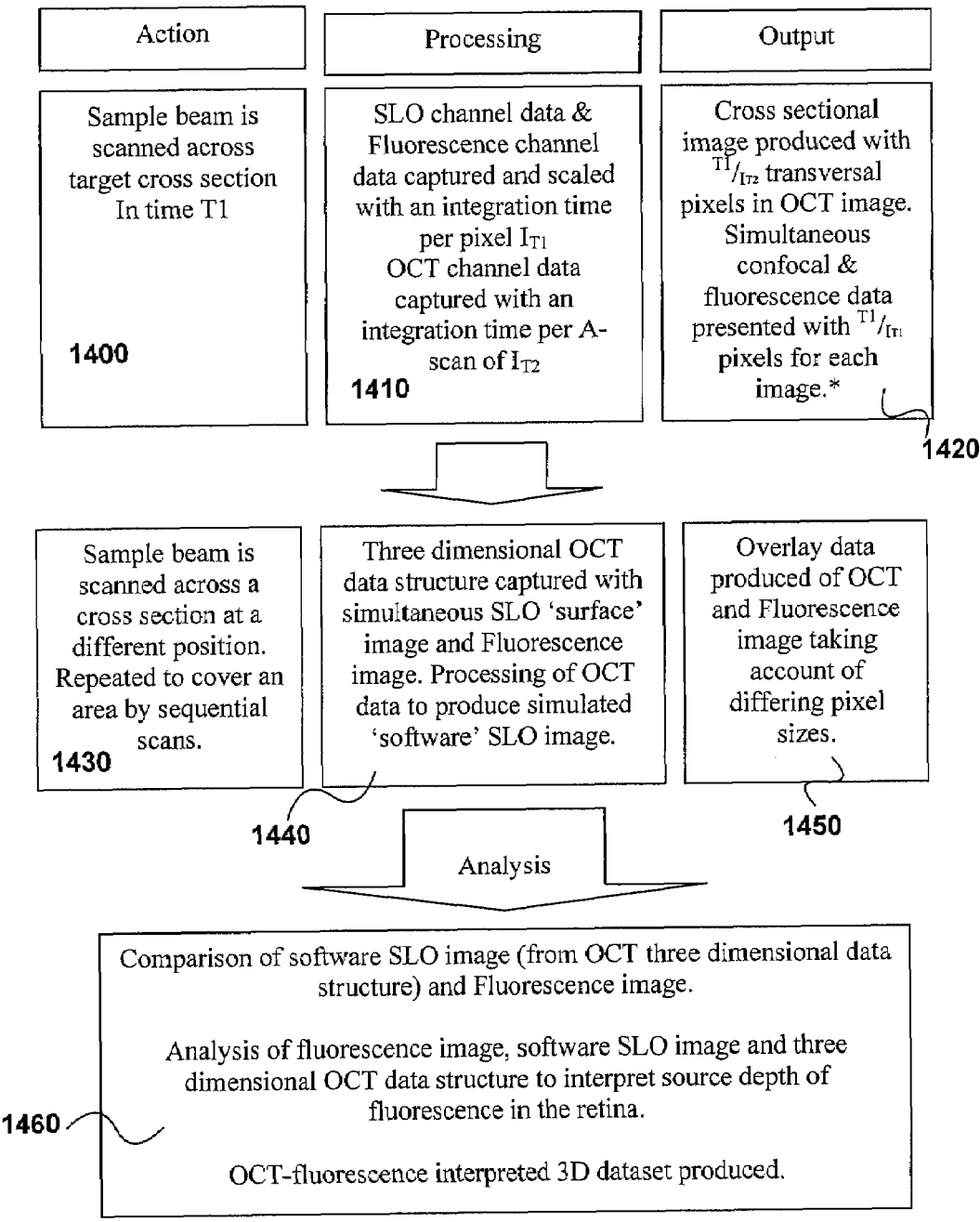
FIG. 14 is a flow chart for implementing fluorescence with a simultaneous Spectral OCT receiver.

Flow charts illustrating the operation of the software for the various aspects of the invention are illustrated in FIGS. 12, 13, and 14, which adopt a frame strategy as shown in FIG. 4. With respect to FIG. 12, it should be noted that the process can be repeated as necessary to display cross sectional OCT data relative to the SLO image.

At step 1220, the sample beam is scanned across the target area in time T1. Next at step 122, the SLO channel data is captured and scaled. At step 1224, the surface image is displayed.

Then at step 226 the sample beam is switched and scanned across a desired cross-sectional plane in time T2 to generate the OCT raw spectral data. The raw spectral data is captured and processed at step 1228, and the OCT image displayed at step 1230.

At steps 1234, 1236, and 1238, steps 1220, 1222, and 1224 are repeated to obtain a new confocal surface image.

At steps 1240, 1242, and 1244, steps 1226, 1228, and 1230 are repeated to obtain another OCT frame.

T1 can be varied so that it could be of the order of T2. A typical setup would use a T1 of between 150 and 250 milliseconds to give an SLO image made from several hundred lines of scanned information to reference a cross sectional OCT image taken between 20 and 250 milliseconds.

FIG. 13 illustrates a diagnostic method wherein a software created SLO image is compared with a hardware created SLO image. AT step 1300, the sample beam is scanned across the target in time T1. Then in step 1310, the SLO channel data is captured and scaled with an integration time per pixel of $I_{T1}$ and the OCT channel data is captured with an integration time per A-scan of $I_{T2}$. A cross sectional image is produced with $_{T1}/I_{T2}$ pixels in the OCT image and simultaneous confocal data is presented with $_{T1}/I_{T1}$ pixels at step 1320.

At step 1330, the sample beam is scanned across a cross section at a different position. This operation is repeated to cover an area by sequential scans. At step 1340, a three dimensional data structure I captured with a simultaneous SLO surface image, and the OCT image is processed to produce a simulated software SLO image. A step 1350, the overlay data is produced from the OCT and SLO hardware taking into account the differing pixel sizes.

The SLO image from the data structure can then be compared with the hardware-created SLO image to create a different image. This image can be used for diagnostic purposes.

In an alternative embodiment, more than one OCT image, as shown in FIG. 4, can be reconstructed between SLO images.

In FIG. 14, at step 1400, the sample beam is scanned across the target in time T1. At step 410, the SLO channel data and fluorescence channel data are captured and scaled with an integration time per pixel $I_{T1}$, and the OCT channel data is captured with an integration time per A-scan of $I_{T2}$. At step 1420, the cross sectional image is produced with $_{T1}/I_{T1}$ transversal pixels in the OCT image. Simultaneous confocal and fluorescence data are presented with $_{T1}/I_{T1}$ pixels for each image.

At step 1400, the sample beam is scanned across a cross section at a different position. At step 1440, a three dimensional data structure is capture with a simultaneous surface image and fluorescence image. The OCT data is processed to produce a simulated software SLO image.

At step 1450, the overlay data is produced by the OCT and fluorescence image taking into account different pixel sizes.

Finally, at step 1460, the images are compared to produce a three dimensional dataset.

The invention claimed is:

1. An optical imaging apparatus for obtaining depth profile information from a transparent object, comprising:
    a spectral optical coherence tomography (OCT) apparatus for generating a sample beam for transversely scanning said object;
    a dual port coupler for combining the sample beam returned from the object with a reference beam to produce respective output beams at a pair of output ports;
    a spectrometer coupled to one of said output ports for producing spectral OCT data from light from said sample beam returned from said object along at least one line extending in a longitudinal direction;
    a confocal detector coupled to the other of said output ports for producing an en-face image of the object in a transverse plane from said light from said sample beam returned from said object;
    a processing unit generating OCT image data along said at least one line from said spectral OCT data;
    said processing unit being configured to display said en-face image;
    a selection device for selecting a point or line on said en-face image; and
    said processing unit being configured to display a portion of said OCT image data corresponding to said point or line of said en-face image.

2. An optical imaging apparatus as claimed in claim 1, wherein said image data is a line of data extending through a selected point on said en-face image to produce an A scan.

3. An optical imaging apparatus as claimed in claim 1, wherein said image data is a frame of data extending through a selected line on said en-face image to produce a B scan sectional display through said line.

4. An optical imaging apparatus as claimed in claim 3, wherein said processing unit is configured to create frames of en-face confocal image data interleaved with frames of OCT image data.

5. An optical imaging apparatus as claimed in claim 1, further comprising a focussing arrangement focuses the light returned from said object onto a common aperture for said confocal detector and said spectrometer.

6. An optical imaging apparatus as claimed in claim 5, wherein said common aperture is provide by an optic fiber.

7. An optical imaging apparatus as claimed in claim 5, wherein said optic fiber is a single mode fiber.

8. An optical imaging apparatus comprising:
    an interferometer for generating a sample beam and a reference beam;
    a scanner for scanning a transparent or semi-transparent object with said sample beam;
    a dual port coupler for combining the sample beam returned from the object with the reference beam to produce respective output beams at a pair of output ports;
    a confocal detector at one of said output ports;
    a spectrometer at the other of said output ports for producing a spectral OCT signal;
    a processing unit for generating OCT image data along at least one line extending longitudinally into the sample from said spectral OCT signal;
    said processing unit being configured to display an en-face confocal image from said confocal detector;
    a selection device for selecting a point or line on said en-face confocal image; and
    said processing unit being configured to display a portion of said OCT image data corresponding to said point or line of said en-face image.

9. Optical imaging apparatus as claimed in claim 8, wherein said coupler is a fiber optic coupler, with optic fiber inputs and outputs.

10. Optical imaging apparatus as claimed in claim 8, wherein the sample and reference beam are carried in optical fibers within the interferometer.

11. Optical imaging apparatus as claimed in claim 8, wherein said confocal image frames are en-face image frames, and said OCT image frames correspond to B-scan sectional images extending in a longitudinal direction.

12. Optical imaging apparatus as claimed in claim 8, wherein said selection device is a computer mouse.

13. Optical imaging apparatus comprising:
    an interferometer for generating a sample beam to scan a sample in a raster pattern;
    a dual port coupler for combining the sample beam returned from the object with a reference beam to produce respective output beams at a pair of output ports;
    a fluorescence detector coupled to one of said output ports for producing a signal from fluorescent light produced within the sample by said sample beam;
    a spectrometer coupled to the other of said output ports for deriving an OCT (optical coherence tomography) signal from beam returned by the sample;
    a processor for producing fluorescent image frames from the signal produced by the fluorescence detector and OCT cross sectional images (B-scans) behind each scanning line of the raster pattern, said OCT cross sectional images being obtained by analyzing the spectral composition of the beam returned by the sample; and
    a display for displaying the fluorescence images and OCT cross sectional images in association with the corresponding fluorescence images.

* * * * *

UNITED STATES PATENT AND TRADEMARK OFFICE
Certificate

Patent No. 7,649,629 B2                                                                         Patented: January 19, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Rogers, Canterbury (GB); Mark Hathaway, Canterbury (GB); and Adrian Podoleanu, Canterbury (GB).

Signed and Sealed this Thirteenth Day of March 2012.

<div style="text-align:right">

TARIFUR R. CHOWDHURY
*Supervisory Patent Examiner*
Art Unit 2886
Technology Center 2800

</div>